United States Patent [19]

Cichanowicz et al.

[11] Patent Number: 4,912,036

[45] Date of Patent: * Mar. 27, 1990

[54] RAPID DIFFERENTIATION OF BACTERIA USING CYCLIC POLYPEPTIDE ANTIBIOTICS

[75] Inventors: Peggy W. Cichanowicz, Pittsford; Robert T. Belly, Webster, both of N.Y.

[73] Assignee: Eastman Kodak Company, Rochester, N.Y.

[*] Notice: The portion of the term of this patent subsequent to Dec. 5, 2006 has been disclaimed.

[21] Appl. No.: 910,703

[22] Filed: Sep. 24, 1986

[51] Int. Cl.$^4$ .............................................. C12Q 1/04
[52] U.S. Cl. ........................................ 435/34; 435/29; 435/39; 435/40; 435/805; 435/810; 435/873
[58] Field of Search ...................... 435/29, 34, 39, 40, 435/805, 810, 873

[56] References Cited

U.S. PATENT DOCUMENTS 4,525,453  6/1985  Guardino et al. .................. 435/34
4,746,607  5/1988  Mura et al. ........................ 435/25

OTHER PUBLICATIONS

Finegold et al, "Bailey and Scott's Diagnostic Microbiology" C. V. Mosby Co., St. Louis 1978, p. 21.
Garrod et al, "Antibiotic and Chemotherapy" Churchill Livingston, Edinburgh and London, 1973, pp 182–187.

Primary Examiner—Robert Benson
Attorney, Agent, or Firm—J. Lanny Tucker

[57] ABSTRACT

Rapid differentiation between viable gram-positive and gram-negative bacteria is accomplished with certain polypeptide antibiotics which are used in combination with a compound which is normally reducible by the bacteria. The antibiotics selectively inhibit the reduction of the reducible compound by gram-positive bacteria but do not substantially affect the reducing capacity of the gram-negative bacteria. The particular antibiotics useful are cyclic polypeptides which affect the function of the cytoplasmic membrane of bacteria. A particular polypeptide antibiotic, polymixin B, will distinguish Proteus bacteria from other gram-negative genera.

23 Claims, No Drawings

RAPID DIFFERENTIATION OF BACTERIA USING CYCLIC POLYPEPTIDE ANTIBIOTICS

FIELD OF THE INVENTION

The present invention relates to clinical chemistry. It particularly relates to a composition, element and method for the differentiation between viable gram-positive and viable gram-negative bacteria.

BACKGROUND OF THE INVENTION

All bacteria can be separated into one of two classes, either gram-positive or gram-negative, based on their gram-stain reaction. The gram-stain reaction is, therefore, a key test in the identification of bacteria. In addition, because of general structural and chemical differences between gram-positive and gram-negative bacteria, a different spectrum of antibiotics is used to treat infections caused by one class than is used to treat infections caused by the other class. Knowledge of the gram reaction of an infecting organism is, therefore, important for determination of appropriate treatment.

Currently, the gram stain reaction is a four-step staining procedure performed on a glass slide containing heat-fixed biological specimens. This procedure is both time consuming and labor intensive. Bartholomew (The Gram Stain, Bact. Rev., 16, pp. 1-29, 1952) has written a comprehensive article describing this procedure. It is well known that gram staining can give varying results and is highly dependent upon precise timing and meticulous technique. Furthermore, the procedure is difficult to automate.

An improved differentiation method using anionic surfactants is described in U.S. Pat. No. 4,525,453 (issued June 25, 1985). According to that reference, anionic surfactants selectively inhibit the ability of gram-positive organisms to reduce certain reducible compounds. One of the surfactants taught as preferred in that reference is marketed under the trademark TERGITOL 7 (Sigma Chemical Co., St. Louis, Missouri).

It has been found, however, that the anionic surfactants taught in the art do not effectively differentiate organisms with a wide range of reducible compounds. For example, TERGITOL 7 is useful with tetrazolium salts, but is not useful with certain reducible intramolecular nucleophilic displacement compounds (identified herein as RIND compounds and defined below). In other words, no clear gram separation was observed using a combination of the anionic surfactants and the RIND compounds.

U.S. Pat. No. 4,525,453 further shows that certain antibiotics which are known to inhibit bacterial growth were not effective to differentiate bacteria when used with the reducible compounds described therein.

It would be desirable to have a differentiation method which is not only rapid and simple, but which can also be used with all types of reducible compounds.

SUMMARY OF THE INVENTION

The problems noted above with known differentiation procedures are avoided with a composition for differentiating between viable gram-positive and gram-negative bacteria comprising:

(a) a compound capable of being reduced to provide a detectable species by both viable gram-positive and gram-negative bacteria in the absence of reduction-inhibiting materials, and (b) a cyclic polypeptide antibiotic which affects the function of the cytoplasmic membrane of the bacteria, the antibiotic being present in an amount sufficient to selectively and substantially inhibit the reduction of the reducible compound by the gram-positive bacteria.

The present invention also provides an analytical element for differentiating between viable gram-positive and gram-negative bacteria comprising an absorbent carrier material and containing:

(a) a compound capable of being reduced to provide a detectable species by both viable gram-positive and gram-negative bacteria in the absence of reduction-inhibiting materials, and (b) a cyclic polypeptide antibiotic which affects the function of the cytoplasmic membrane of the bacteria, the antibiotic being present in an amount sufficient to selectively and substantially inhibit the reduction of the reducible compound by the gram-positive bacteria.

Further, a method for differentiating between viable gram-positive and gram-negative bacteria comprises the steps of:

A. mixing a liquid suspected of containing viable gram-positive and gram-negative bacteria with (a) a compound capable of being reduced to provide a detectable species by both viable gram-positive and gram-negative bacteria in the absence of reduction-inhibiting materials, and (b) a cyclic polypeptide antibiotic which affects the function of the cytoplasmic membrane of the bacteria, the antibiotic being present in an amount sufficient to selectively and substantially inhibit the reduction of the reducible compound by the gram-positive bacteria, and B. determining the detectable species resulting from the presence of the gram-negative bacteria.

The present invention provides a rapid, simple and relatively inexpensive means for differentiating the gram type of viable bacteria. This invention avoids the undesirably tedious features of standard gram stain techniques. Further, a wide variety of reducible compounds can be used thereby giving greater flexibility in the assay. For example, such flexibility allows the use of dyes which have high sensitivity, are less toxic to bacteria or which can be detected in spectral regions not affected by potential interferents found in biological fluids.

These advantages are achieved by using cyclic polypeptide antibiotics which affect the cytoplasmic membrane of bacteria in combination with a reducible compound. The antibiotics are present in an amount to selectively and substantially inhibit the reducing capacity of the gram-positive bacteria while the reductive capacity of the gram-negative microorganisms is substantially unaffected. It was further found that the cyclic polypeptide antibiotic polymixin B will distinguish Proteus bacteria from other gram-negative genera.

DETAILED DESCRIPTION OF THE INVENTION

The antibiotics useful in the practice of this invention are those known in the art as cyclic polypeptides. However, not every cyclic polypeptide antibiotic is useful in the practice of this invention. Useful cyclic polypeptide antibiotics are those which affect the function of the cytoplasmic membrane of bacteria as opposed to antibiotics which interfere with nucleic acid or protein biosynthesis or which interfere with cell wall biosynthesis. Such materials are described in a text by R. Reiner entitled Antibiotics, Thieme-Stratton, New York, 1982 e.g. at pages 57, 60 and 116–118. Cyclic polypeptides useful in the practice of this invention are generally understood to be cyclic antibiotics having a multiplicity (two or more) of peptide linkages. A more detailed description of such compounds and methods of their preparation are provided in Chapter 5 (pp. 95–145) of Biochemistry and Genetic Regulation of Commercially Important Antibiotics, edited by Leo. C. Vining, Addison-Wesley Publishing, Reading, Massachusetts, U.S.A., 1983 and the references noted therein.

Without intending to be so limited in the practice of this invention, the following cyclic polypeptide antibiotics are useful in the practice of this invention: gramicidin S, tyrocidin, subtilin and polymixin B. Preferred antibiotics include gramicidin S, tyrocidin and polymixin B.

It will be understood by those skilled in the art that for each antibiotic useful in the present invention there will be an optimal concentration range (depending upon the purity and potency of the antibiotic) and optimal environmental conditions for substantially inhibiting the reductive capability of gram-positive bacteria and for differentiation. In general, the amount of antibiotic needed to selectively and substantially inhibit the reduction of the reducible compound (described below) by gram-positive bacteria can be determined readily by mixing about $10^7$ cells/ml of a gram-positive bacterium (for example, S. aureus), an antibiotic (about $10^{-4}$ molar) and a reducible compound (about 0.005 molar) at pH 7.5. If the reducible compound is reduced producing a detectable change, the amount of antibiotic is increased accordingly in further tests until no detectable change is observed.

Further, there may be a few exceptions to the selective inhibitory action of the polypeptide antibiotics to certain gram-positive bacteria. Further, there may be a few exceptions to the affect of the antibiotic on gram-negative bacteria. For example, in one embodiment, the cyclic polypeptide antibiotic polymixin B can be used to substantially inhibit the reductive capacity of gram-negative bacteria except for *Proteus genera*. Therefore, polymixin B can be used in a method to differentiate a *Proteus* species, such as *P. vulgaris*, from other gram-negative bacteria.

However, other than the exceptions noted above, the cyclic polypeptide antibiotics described herein generally exhibit the selective inhibition described herein.

The reducible compound useful in the practice of this invention can be any material that, in its oxidized form, is capable of being reduced by both viable gram-positive and gram-negative microorganisms, in the absence of any reduction-inhibiting materials, to produce a detectable species. Such species can be detected by any suitable means including potentiometric or radiometric means. Preferably, as defined below, the species is detected with radio-metric means.

A partial listing of various detectable species that are directly detectable by radiometric means includes colorimetrically detectable materials, such as chromogens, radiation emission materials, such as fluorogens, chemiluminescent materials, radioactive isotopes, phosphorescent materials, etc.

The use of dyes or dye precursors presents several possibilities for detection: (1) a colored species can become colorless or undergo a shift in absorption, (2) a colorless species, i.e. a dye precursor can form a colored species, or (3) a species containing a shiftable detectable species can release the shiftable detectable species. Alternative (3) is preferred in the practice of this invention.

Examples of dyes or dye precursors that can be used as reducible compounds include methylene blue, dichloroindophenol, resazurin, and various tetrazolium compounds, such as 3-(4,5-dimethyl-2-thiazolyl)-2,5-diphenyl-2H-tetrazolium bromide, 2,3,5-triphenyl-2H-tetrazolium chloride, tetranitro blue, tetrazolium chloride and nitrotetrazolium violet, and others described, for example in U.S. Pat. No. 4,525,453, noted above.

More particularly, the reducible compounds useful in this invention have the structure $CAR-(R^1)_n$ wherein CAR— represents a substituted or unsubstituted aromatic or quinone nucleus, $R^1$ is a moiety comprising a shiftable detectable species defined herein, and n is 1 or 2. The term "shiftable detectable species" can be defined as a chromogen moiety which has a first spectral absorption band when attached to the reducible compound and a second absorption band when released from the reducible compound, or a fluorogen moiety which has first spectral absorption and emission bands when attached to the reducible compound and second spectral absorption and emission bands when released. Examples of such nuclei are presented below. Further, when $R^1$ is replaced by H, $CAR-(H)_n$ has a reduction potential ($E_{\frac{1}{2}}$) of either at least about $+100$ mV when measured in water, or of at least about $-650$ mV when measured in acetonitrile. This $E_{\frac{1}{2}}$ value facilitates the reduction and subsequent release of the detectable species from the compound at physiological pH (that is, 9 or less). Such measurements are made according to standard electrochemical techniques using either differential pulse polarography or cyclic voltametry (see, for example, Sawyer and Roberts, Jr., Experimental Electrochemistry for Chemists, John Wiley & Sons, New York, 1974). Preferably, the $E_{\frac{1}{2}}$ is from about $+100$ mV to about $+400$ mV as measured in water, or from about $-650$ to about $-300$ mV as measured in acetonitrile. Both ranges are given because some of the reducible compounds are best measured in water whereas others are best measured in acetonitrile. Further details of measuring the $E_{\frac{1}{2}}$ are described below prior to Table I. The desired $E_{\frac{1}{2}}$ is achieved by appropriate electron withdrawing groups on the CAR— nucleus, or by a strained fused ring attached to the nucleus or by a combination of both.

In one embodiment, the reducible compounds can be reduced to provide a detectable species through quinone methide formation, similar to the description by Van de Sande in Angew. Chem. Int. Ed. Engl. 22, pp. 191–209 (1983) and U.S. Pat. No. 4,232,107 (issued Nov. 4, 1980 to Janssens), but which have the desired $E_{\frac{1}{2}}$ properties.

In another embodiment, useful reducible compounds include sulfilimides and sulfenylsulfonamides similar to those described on page 206 of the Van de Sande reference noted above, but which have the desired $E_{\frac{1}{2}}$ properties.

In a preferred embodiment, the reducible compounds are RIND compounds, that is, reducible compounds capable of undergoing intramolecular nucleophilic displacement at physiological pH to release one or more detectable species when a nucleophilic group is generated by at least a one electron reduction of the compound. In other words, such displacement occurs when the RIND compound is reduced by a suitable reductant which provides the necessary electron(s) (described in more detail below). The release of detectable species is very efficient in that, for most of the preferred compounds, at least 50% of the detectable species is provided within 30 minutes at about pH 7.

The term "intramolecular nucleophilic displacement" refers to a reaction in which a nucleophilic center on a molecule reacts at another site in the molecule, which site is an electrophilic center, to effect displacement of a group or atom attached to the electrophilic center. Generally, the RIND compounds useful in this invention have the nucleophilic and electrophilic groups juxtaposed in the three-dimensional configuration of the molecule in close proximity whereby the intramolecular reaction can take place and a ring is formed having from 4 to 7 atoms, and preferably having 5 or 6 atoms.

Particularly useful RIND compounds are those represented by the structure CAR—$R^1$ wherein CAR— is

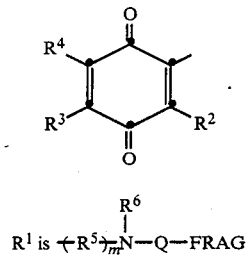

$R^1$ is $+R^5\!\!\rightarrow_m\!\!N-Q-FRAG$ wherein m is 0 or 1, and preferably 1. $R^5$ is substituted or unsubstituted alkylene, preferably of 1 or 2 carbon atoms in the backbone (for example, methylene, ethylene or alkoxymethylene). Most preferably, $R^5$ is methylene. Q is carbonyl or thiocarbonyl and preferably carbonyl.

$R^6$ is substituted or unsubstituted alkyl, preferably of 1 to 40 carbon atoms (for example, methyl, ethyl, n-propyl, isopropyl, t-butyl, hexyl, decyl, lauryl, benzyl or n-propyl-n-butylether), substituted or unsubstituted cycloalkyl, preferably of 4 to 40 carbon atoms (for example, cyclobutyl, cyclohexyl or 4-methylcyclohexyl), substituted or unsubstituted heterocycle, preferably of 5 to 40 atoms (carbon and heteroatoms, for example, pyridyl), or substituted or unsubstituted aryl, preferably of 6 to 40 carbon atoms (e.g. phenyl, xylyl, naphthyl, p-nitrophenyl, anthryl, p-t-butoxyphenyl or p-carboxyphenyl). Preferably, $R^6$ is substituted or unsubstituted alkyl, or substituted or unsubstituted aryl as defined above.

FRAG is a shiftable detectable species as defined above. The specific composition of FRAG can vary considerably depending upon the type of detectable species desired and upon the particular detection means employed. The detectable species can be a material which is directly detectable by a suitable means, as well as a material which can react with other substances, for example, analytes, enzymes or other reagents to provide a detectable species.

Particularly useful detectable species are chromogens and fluorogens. Examples of useful classes of chromogens are azo, azomethine, nitrophenol, indophenol, indoaniline and triarylmethane dyes, and others known in the art, with azo dyes being preferred. Examples of useful classes of fluorogens are coumarin, umbelliferone, phenalenone and benzphenalenone, 4-oxo-4-H-benz-[d,e]anthracenes, fluorescein and rhodamine fluorescent dyes, and others known in the art. Phenalenone dyes are particularly useful.

Useful phosphorescent species include such phosphors as 2′,5′-dibromofluorescein and 4′,5′-di-iodofluorescein. A useful chemiluminescent species is luciferin.

FRAG is linked to Q by means of a single bond through a bivalent monoatom linkage which is a part of FRAG. Preferably, the monoatom linkage is oxy, thio or seleno when FRAG is a chromogen and oxy or thio when FRAG is a fluorogen. Most preferably, the linkage is oxy.

$R^2$, $R^3$ and $R^4$ in the above quinone structure are independently hydrogen, substituted or unsubstituted alkyl of 1 to 40 carbon atoms (for example, methyl, ethyl, hydroxymethyl or methoxymethyl) substituted or unsubstituted aryl (for example, phenyl, naphthyl, methylnaphthyl, p-nitrophenyl, m-methoxyphenyl or p-carboxyphenyl) or an electron withdrawing group which generally has a positive Hammett sigma value, and preferably has a sigma value greater than about 0.06. At least one of $R^2$, $R^3$ and $R^4$ is an electron withdrawing group. Hammett sigma values are calculated in accordance with standard procedures described, e.g. in Steric Effects in Organic Chemistry, John Wiley and Sons, Inc., 1956, pp. 570–574 and Progress in Physical Organic Chemistry, Vol. 2, Interscience Publishers, 1964, pp. 333–339. Representative electron withdrawing groups having positive Hammett sigma values include cyano, carboxy, nitro, halo (for example, fluoro, bromo, chloro or iodo), trihalomethyl (for example, trifluoromethyl or trichloromethyl), trialkylammonium, carbonyl, carbamoyl, sulfonyl, sulfamoyl, esters and others known in the art, or alkyl or aryl groups (defined above) substituted with one or more of these electron withdrawing groups. Preferred electron withdrawing groups include p-nitrophenyl, m-nitrophenyl, p-cyanophenyl and 2,5-dichlorophenyl. Aryl groups with methoxy or acetamido groups in the meta position are also useful.

$R^3$ can also be $R^1$ thereby potentially providing a 2:1 molar ratio of detectable species molecules to original RIND compound molecules.

Alternatively, $R^3$ and $R^4$, taken together, can represent the carbon atoms necessary to complete a substituted or unsubstituted strained fused carbocyclic ring attached to the quinone nucleus. Strained fused rings are known in the art (for example, Rieke et al, Tetrahedron Letters, 50, pp. 4381–4384, 1969). For example, such a ring (mono- or bicyclic) can have from 4 to 8 carbon atoms in the backbone. Preferably, the ring is a 5-membered mono- ring, or a 7- or 8-membered bicyclic ring.

Particularly useful reducible compounds are those described and claimed in copending and commonly assigned U.S. application Ser. No. 868,855, filed May 30, 1986, by Mura et al and entitled WATER-COMPATIBLE REDUCIBLE COMPOUNDS AND THEIR USE IN ANALYTICAL COMPOSITIONS AND METHODS.

Representative RIND compounds are listed in Table I below in reference to the following structure:

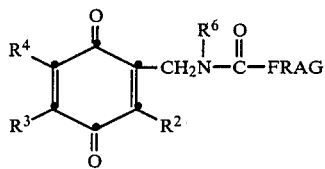

The $E_{\frac{1}{2}}$ values in Table I were determined for the quinone nucleus of this structure having a hydrogen atom in place of

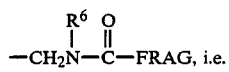

-continued

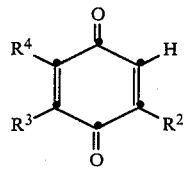

The $E_{\frac{1}{2}}$ values (where available) were measured in an aqueous emulsion of the quinone dissolved in N,N-dimethylformamide, a nonionic surfactant (TRITON X-100) and sodium phosphate buffer (pH 7). A standard calomel electrode was used as a standard. Some $E_{\frac{1}{2}}$ values (denoted by *) were measured in acetonitrile using a saturated calomel electrode as a standard. $E_{\frac{1}{2}}$ values not available are denoted by "NA".

TABLE I

| RIND Compound | $R^6$ | $R^2$ | $R^4$ | $R^3$ | FRAG | $E_{\frac{1}{2}}$ (mV) |
|---|---|---|---|---|---|---|
| I. | —CH₃ | 4-(isopropyl)-C₆H₄-SO₂NHC₁₀H₂₁ | same as $R^2$ | —CH₂N(CH₃)—C(O)—FRAG | naphthol-azo-(2-SO₂CH₃-4-NO₂-phenyl), with 8-NHSO₂-(3-SO₂NH₂-phenyl) | −528* |
| II. | —CH₃ | 4-NO₂-C₆H₄- | same as $R^2$ | " | " | +236 |
| III. | —CH₃ | 4-(isopropyl)-C₆H₄-SO₂NHCH(CH₃)₂ | same as $R^2$ | " | " | NA |
| IV. | —CH₃ | C₆H₅- | same as $R^2$ | " | " | −460* |
| V. | —CH₃ | 2-NO₂-C₆H₄- | $R^3$ and $R^4$ together form a ring | | " | +214 |
| VI. | —CH₃ | C₆H₅- | | " | " | +180 |

TABLE I-continued

| RIND Compound | R⁶ | R² | R⁴ | R³ | FRAG | E½ (mV) |
|---|---|---|---|---|---|---|
| VII. | —CH₃ | 4-NO₂-phenyl | | " | " | +236 |
| VIII. | —CH₃ | 4-SO₂NHCH(CH₃)₂-phenyl | | " | " | +212 |
| IX. | —CH₃ | 4-CN-phenyl | | " | " | +220 |
| X. | —CH₃ | 4-OCH₃-phenyl | | " | " | +154 |
| XI. | —CH₃ | 3,5-dinitrophenyl | | " | " | +186 |
| XII. | —CH₃ | 4-C(O)C₁₀H₂₁-phenyl | | " | " | +206 |
| XIII. | —CH₃ | 4-C(O)CH₃-phenyl | | " | " | +212 |

TABLE I-continued

| RIND Compound | R⁶ | R² | R⁴ | R³ | FRAG | $E_{\frac{1}{2}}$ (mV) |
|---|---|---|---|---|---|---|
| XIV. | —CH₃ | 4-Br-phenyl | | | " | +192 |
| XV. | —CH₃ | —H | | | " | +213 |
| XVI. | —C₁₂H₂₅ | 4-CN-phenyl | | | " | +220 |
| XVII. | —CH₃ | " | R³ and R⁴ together form cyclopentadiene | | " | +240 |
| XVIII. | —CH₃ | 4-NO₂-phenyl | t-butyl | —H | " | NA |
| XIX. | —CH₃ | phenyl | R³ and R⁴ together form | | " | +242 |
| XX. | —CH₃ | " | R³ and R⁴ together form | | " | +222 |

TABLE I-continued
| RIND Compound | $R^6$ | $R^2$ | $R^4$ | $R^3$ | FRAG | $E_{\frac{1}{2}}$ (mV) |
|---|---|---|---|---|---|---|
| XXI. | —CH$_3$ |  | same as $R^2$ | —CH$_2$N(CH$_3$)—C(O)—FRAG |  | −528* |
| XXII. | —CH$_3$ | " | " | " |  | −528* |
| XXIII. | —CH$_3$ | 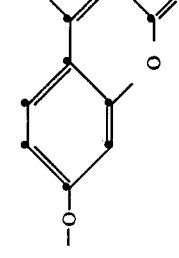 | $R^3$ and $R^4$ together form 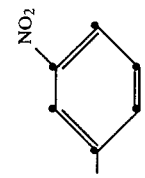 | | " | +214 |
| XXIV. | —CH$_3$ | 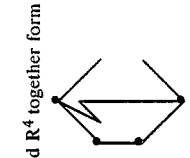 | $R^3$ and $R^4$ together form 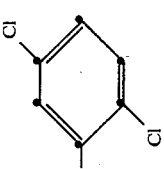 | | 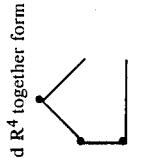 | +236 |

TABLE I-continued

| RIND Compound | R$^6$ | R$^2$ | R$^4$ | R$^3$ | FRAG | E$_{\frac{1}{2}}$ (mV) |
|---|---|---|---|---|---|---|
| XXV. | —CH$_3$ | -phenyl | R$^3$ and R$^4$ together form —CH(C$_{12}$H$_{25}$)— branched | | " | +222 |
| XXVI. | —CH$_3$ | " | —CH$_3$ | —CH$_3$ | " | +144 |
| XXVII. | —CH$_3$ | " | R$^3$ and R$^4$ together form (CH$_3$)—CH—CH$_2$—CH(CH$_3$) | | " | +122 |
| XXVIII. | —CH$_3$ | " | R$^3$ and R$^4$ together form cyclic with (CH$_3$)$_2$HC— and CH$_3$ substituents | | " | +174 |
| XXIX. | —CH$_3$ | 4-cyanophenyl | R$^3$ and R$^4$ together form cyclohexyl | | " | +220 |
| XXX. | —CH$_3$ | phenyl | R$^3$ and R$^4$ together form cyclopentyl | | " | +222 |

TABLE I-continued

| RIND Compound | R⁶ | R² | R⁴ | R³ | FRAG | E₁/₂ (mV) |
|---|---|---|---|---|---|---|
| XXXI. | —CH₃ | 2,4-dichlorophenyl | | | " | +236 |
| XXXII. | —CH₃ | 2-nitrophenyl | R³ and R⁴ together form | | " | +214 |
| XXXIII. | —CH₃ | 4-nitrophenyl | " | | " | +236 |
| XXXIV. | —CH₃ | 4-SO₂NH(CH₃)₂ phenyl | " | | " | +212 |
| XXXV. | —CH₃ | 4-COOH phenyl | " | | " | +220 |

RIND compounds IX, XXIX and XXXV are preferred in the practice of this invention.

The RIND compounds useful in the practice of this invention are prepared using a sequence of individually known reactions. Generally, the preparation sequence includes the following general steps: (1) preparation of the substituted hydroquinone, (2) oxazine ring formation, (3) oxazine ring opening, (4) preparation of the carbamoyl chloride, and (5) reaction of a compound from which the FRAG moiety is derived with the carbamoyl chloride. Preparation of these compounds is described in more detail in co-pending and commonly assigned U.S. Ser. No. 824,766, filed Jan. 31, 1986 by Belly et al and entitled REDUCIBLE COMPOUNDS AND ANALYTICAL COMPOSITIONS, ELEMENTS AND METHODS UTILIZING SAME and in U.S. Ser. No. 868,855 of Mura et al, noted above.

Other RIND compounds useful in the practice of this invention include those having the appropriate $E_{\frac{1}{2}}$ values and the structure CAR—$(R^1)_n$ wherein:

(1) CAR— is a substituted or unsubstituted nucleus of a 1,2-naphthoquinone, 1,2-, 1,4- or 9,10-anthraquinone, 4,4'-diphenoquinone, azuloquinone or 1,6-[10]-anulenoquinone wherein $R^1$ is attached to the nucleus one carbon atom distant or in the peri position from one of the oxo groups of the nucleus. The nucleus can be substituted with one or more electron withdrawing groups as described above for $R^2$ or have one or more strained fused rings as described above for $R^3$ and $R^4$. $R^1$ is

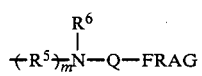

as defined above, and n is an integer of 1 or 2.

(2) CAR— is

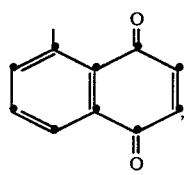

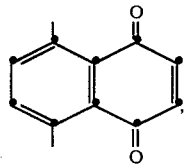

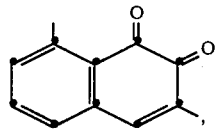

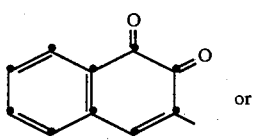

or

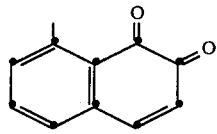

any of which can be substituted with one or more electron withdrawing groups as described above for $R^2$, $R^3$ and $R^4$. $R^1$ is

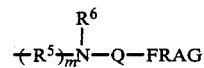

as defined above, and n is 1 or 2.

(3) CAR— is a substituted or unsubstituted nitrobenzenoid nucleus of the structure

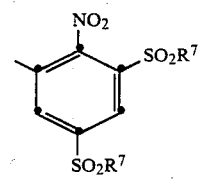

wherein $R^7$ is substituted or unsubstituted alkyl of 1 to 20 carbon atoms (for example, methyl, ethyl, methoxymethyl, isopropyl, dodecyl, hexadecyl or octadecyl), and $R^1$ is

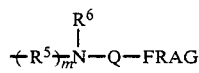

as defined above and n is 1. These compounds are similar to some described in U.S. Pat. No. 4,139,379 (noted above).

In another embodiment, the reducible compound can be a cobalt (III) complex, as described in copending and commonly assigned U.S.S.N. 890,050, filed by Schmittou July 28, 1986 and entitled COBALT CONTAINING REAGENTS AND METHODS FOR THE DETERMINATION OF ANALYTES IN AQUEOUS FLUIDS.

All of these reducible compounds can be prepared using techniques and starting materials known in the art or readily apparent to a skilled synthetic chemist.

Generally, the reducible compounds described herein have limited water solubility. Hence, it is best, when using them in an aqueous environment, to prepare a dispersion of the compound prior to use, for example, in a coating formulation. Such dispersions generally comprise the reducible compound, an aqueous buffer solution and either a solubilizing surfactant or a water-miscible organic solvent for the compound, or both. Surfactants which are useful in the practice of this invention include any surfactants which do not inhibit compound reduction. Nonionic surfactants are particularly useful.

Useful water-miscible organic solvents include alcohols (for example, methanol, ethanol or propanol), N,N-dimethylformamide, dimethyl sulfoxide, acetonitrile, hexamethylenephosphoramide and others known in the art. The particular solvent to be used for a particular reducible compound can be readily determined by routine experimentation.

A dispersion can be prepared in the following general manner. The reducible compound is dissolved in the water-miscible solvent at a concentration which depends upon its molecular weight, but generally at from about 1 to about 100, and preferably from about 5 to about 80, mg per ml of solvent. The resulting solution is then mixed with a suitable surfactant in an amount generally of from about 0.1 to about 24, and preferably from about 0.5 to about 10, ml surfactant per ml of dispersion. This preparation is generally carried out at room temperature.

When using the water-compatible reducible compounds described above, compositions containing same can be prepared without the use of surfactants. The compounds can be dissolved in an appropriate organic solvent, and the resulting solution added directly to a buffer.

The compositions of this invention generally contain a buffer in an amount effective to maintain a pH of 9 or less. The concentration of buffer in the dispersion can vary widely, but is generally from about 0.01 to about 0.1 molar. Representative buffers include phosphates, and others reported by Good et al in Biochemistry, 5, 467 (1966), and Anal. Biochem., 104, 300 (1980).

The present invention is useful for differentiation of viable gram-positive and gram-negative bacteria in any fluid specimen including wastewater, food stuffs, manufacturing solutions and biological fluids. It is particularly useful in differentiation of bacteria in human biological fluids, such as urine, serum, whole blood, sputum, spinal fluid, etc. Organisms commonly found in the human urinary tract are advantageously differentiated with this invention.

Differentiation of viable bacteria according to this invention is preferably carried out in the presence of an electron transfer agent (identified herein as an ETA). The presence of an ETA provides more rapid dye release. It is a mobile compound which acts as an intermediary between the microorganism and the reducible compound. The ETA is generally present at a concentration that is dependant upon the concentration of the reducible compound, but preferably at a concentration of from about $1 \times 10^{-7}$ molar to about $1 \times 10^{-3}$ molar.

ETA compounds useful in the practice of this invention include phenazine methosulfate, phenazine ethosulfate and similar compounds known to one skilled in the art. Combinations of different ETA compounds can be used if desired.

Preferred ETA compounds are those which are the subject of copending and commonly assigned U.S. Ser. No. 699,374 of Mura et al filed Feb. 7, 1985, now U.S. Pat. No. 4,746,607. In general, those compounds are substituted benzo- and naphthoquinones. Examples of this class of quinones include 2,3-dimethyl-5-hydroxymethyl-1,4-benzoquinone, 2,5-dimethoxy-1,4-benzoquinone, 2,3,5-trimethyl-1,4-benzoquinone, 2,6-dimethoxy-1,4-benzoquinone, 2,3-dimethoxy-5-methyl-1,4-benzoquinone, 2-hydroxymethyl-1,4-naphthoquinone and 2-(2-hydroxyethyl)-1,4-naphthoquinone. Substituted 1,2-benzoquinones, such as 4,5-dimethoxy-1,2-benzoquinone, are also useful in the practice of this invention.

The differentiation of viable cells is often carried out in the presence of a nutrient for those cells although its presence is not essential. Any nutrient medium can be used which contains useful carbon, and optionally nitrogen, sources. Suitable nutrient media having proper components and pH are well known in the art.

The cyclic polypeptide antibiotic concentration can also vary widely depending upon the antibiotic and reducible compound used, as well as the particular bacteria being differentiated as long as it is sufficient to inhibit the reductive capacity of the gram-positive bacteria. In the case of differentiation of a Proteus species from other gram-negative bacteria, polymixin B is present in an amount sufficient to inhibit the reductive capacity of the gram-negative bacteria other than Proteus species. However, in either case, the antibiotic is generally present in an amount of at least about $10^{-5}$, and preferably from about $10^{-4}$ to about $10^{-2}$, molar. The other preferred but optional materials are present in amounts which one skilled in the art can readily determine with routine experimentation.

The method of this invention can conveniently be carried out in standard laboratory glassware, for example, using test tubes, microtitration plates or slides. A sample of the fluid suspected of containing the bacteria is mixed with the reducible compound, the cyclic polypeptide antibiotic and any other materials as required. After an appropriate time for microbial reaction and reduction of the reducible compound by gram-negative bacteria, the amount of resulting detectable species is measured with suitable equipment and procedures.

In some instances, it may be desirable to mix and incubate the test sample containing bacteria and the antibiotic in a pretreatment step prior to mixing with the reducible compound therein. This may reduce the amount of background density encountered with some assays due to the presence of impurities in the antibiotics. Another pretreatment step to eliminate interferents may also be desirable.

The method can also be carried out by contacting a porous absorbent material, for example, paper strip, containing a test sample with a dispersion of the reducible compound and polypeptide antibiotic. The bacteria in the test sample can intermingle with the dispersion and initiate the analytical reactions needed for differentiation.

In one embodiment, a test strip can be used as a convenient way to carry measured amounts of reagent(s) to the test solution in a solution assay. The test strip is placed into a solution that might already contain the analyte to be measured. The reagents dissolve from the test strip into the solution so as to form the reaction solution. In preferred embodiments of the test strips of the present invention, the reagents are carried in a water soluble binder. When the test strip is immersed into the solution, the binder dissolves releasing the reagents. Useful water soluble polymers include poly(N-vinyl-2-pyrrolidone) and poly(acrylamide-co-N-vinyl-2-pyrrolidone) (90:10 weight ratio).

Alternatively, the method of this invention can be practiced with a dry analytical element. Such an element can be a absorbent carrier material, i.e. a thin sheet or strip of self-supporting absorbent or bibulous material, such as filter paper or strips, which contains the reducible compound and antibiotic or a dried residue of same. Such elements are known in the art as test strips, diagnostic elements, dip sticks and diagnostic agents.

When employed in dry analytical elements, the reducible compounds and antibiotics described herein can be incorporated into a suitable absorbent carrier material by imbibition or impregnation, or can be coated on a suitable absorbent material. Useful carrier materials are insoluble and maintain their structural integrity when exposed to water or physiological fluids such as urine or serum. Useful carrier materials can be prepared from paper, porous particulate structures, cellulose, porous polymeric films, glass fiber, woven and nonwoven fabrics (synthetic and nonsynthetic) and the like. Useful materials and procedures for making such elements are well known in the art as exemplified by U.S. Pat. Nos. 3,092,465 (issued June 4, 1963 to Adams et al), 3,802,842 (issued Apr. 9, 1974 to Lange et al), 3,915,647 (issued Oct. 28, 1975 to Wright), 3,917,453 (issued Nov. 4, 1975 to Milligan et al), 3,936,357 (issued Feb. 3, 1976 to Milligan et al), 4,248,829 (issued Feb. 3, 1981 to Kitajima et al), 4,255,384 (issued Mar. 10, 1981 Kitajima et al), and 4,270,920 (issued June 2, 1981 to Kondo et al), and U.K. Pat. No. 2,052,057 (published Jan. 21, 1981).

In one embodiment, an analytical element comprises a nonporous support having thereon at least one porous spreading zone as the absorbent carrier material. The reducible compound or antibiotic can be in the spreading zone or in a different zone (for example, a reagent zone, registration zone or hydrophilic zone). The spreading zone can be prepared from any suitable fibrous or non-fibrous material or mixtures of either or both.

The spreading zone can be prepared using fibrous materials, either mixed with a suitable binder material or woven into a fabric, as described in U.S. Pat. No. 4,292,272 (issued Sept. 29, 1981 to Kitajima et al), from polymeric compositions or particulate materials, with or without binding adhesives, as described in U.S. Pat. Nos. 3,992,158 (issued Nov. 16, 1976 to Przybylowicz et al), 4,258,001 (issued Mar. 24, 1981 to Pierce et al) and 4,430,436 (issued Feb. 7, 1984 to Koyama et al) and Japanese Patent Publication 57(1982)-101760 (published June. 24, 1982). It is desired that the spreading zones be isotropically porous, meaning that the porosity is the same in each direction in the zone as created by interconnected spaces or pores between particles, fibers or polymeric strands.

Suitable supports can be any suitable dimensionally stable, and preferably, transparent (that is, radiation transmissive) film or sheet material which transmits electromagnetic radiation of a wavelength between about 200 and about 900 nm. A support of choice for a particular element should be compatible with the intended mode of detection (for example, reflection, fluorescence or transmission spectroscopy) and inert to chemical reagents and liquid samples used in the assay. Useful support materials include polystyrene, polyesters, polycarbonates, cellulose esters and others known in the art.

The elements can have a multiplicity of zones which can be superposed layers or distinct areas in the same layer. The reducible compound, antibiotic and any other reagents can be located in the same or different zones within the element. Element configurations are well known in the art, as described, for example in the patents noted above.

A variety of different elements can be prepared in accordance with the present invention. Elements can be configured in a variety of forms, including elongated tapes of any desired width, sheets, slides or chips.

The method carried out with an element can be manual or automated. In general, differentiation is made by taking the element from a supply roll, chip packet or other source and contacting it with a sample (for example, up to 200 μl) of the liquid to be tested so that the sample mixes with the reagents in the element. Such contact can be accomplished in any suitable manner, for example, dipping or immersing the element into the sample or, preferably, by spotting the element by hand or machine with one or more drops of the sample with a suitable dispensing means.

After sample application, the element can be exposed to conditioning, such as incubation, heating or the like, that may be desirable to quicken or otherwise facilitate obtaining any test result. Detection of viable gram-negative bacteria is achieved when the reducible compound is reduced releasing a species which can be detected in a suitable manner. In some instances, the antibiotic and test sample may be mixed and pretreated (as described above for a solution assay) prior to applying the mixture to the element containing the reducible compound.

Materials used in the following examples were obtained as follows:

gram-negative microorganisms *Enterobacter cloacae* (ATCC 23355), *Escherichia coli* (ATCC 25922), *Proteus vulgaris* (ATCC 13315), *Klebsiella pneumoniae* (ATCC 13883) and *Pseudomonas aeruginosa* (ATCC 27853), and gram-positive microorganisms *Staphylococcus aureus* (ATCC 25923), and *Streptococcus pyogenes* (ATCC 19615), and brain heart infusion (BHI) broth from Difco Laboratories (Detroit, Michigan, U.S.A.),

*Streptococcus faecalis* was isolated from a clinical urine specimen obtained from a local hospital, gramicidin S and TERGITOL 7 anionic surfactant from Sigma Chemical Co. (St. Louis, Missouri, U.S.A.), subtilin from K/K Laboratories Inc. (Plainview, New Jersey, U.S.A.), tyrocidin from Accurate Chemical and Scientific Corp. (Westbury, New York, U.S.A.), ZONYL FSN surfactant from DuPont Co. (Wilmington, Delaware, U.S.A.), TRITON X-100 nonionic surfactant from Rohm and Haas (Philadelphia, Pennsylvania, U.S.A.), trimethyl-1,4-benzoquinone derived from the corresponding hydroquinone purchased from Aldrich Chemical Co. (Milwaukee, Wisconsin, U.S.A.), and the remainder from Eastman Kodak Co. (Rochester, New York, U.S.A.) or prepared using known starting materials and procedures.

In practicing the method of this invention, the following procedures were carried out:

Bacterial suspensions were prepared by growing the cells in BHT broth to stationary phase overnight at 37° C. *P. auruginosa* was grown with agitation. About 40 ml of each overnight culture was centrifuged, decanted and washed once with 0.05 molar potassium phosphate buffer or 0.05 molar N-2-hydroxy-ethylpiperazine-N'-2-ethanesulfonic acid (HEPES) buffer, pH 7.8, and resuspended in buffer.

Dispersions containing RIND compounds were prepared by dissolving the RIND compound in N,N-dimethylformamide (DMF) at 16 mg compound per ml of solvent. An aliquot (250 μl) of the resulting solution was added to 500 μl of TRITON X-100 surfactant. This mixture was then added dropwise with stirring to 25 ml of 0.05 molar HEPES buffer. A dispersion of RIND XXIX was prepared similarly except that DMF was acidified with 0.1% sulfuric acid. Compositions containing water-compatible RIND compounds were prepared as described above except the surfactant was omitted.

Urine samples for Example 7 below were prepared as follows. Clinical urine specimens, which had been refrigerated up to 24 hours, were obtained from area hospitals. Samples of each (10 ml) were centrifuged at 2500 rpm for 10 minutes. After decantation, the pellet from each sample was suspended in 10 ml of buffer (0.05 molar potassium phosphate or HEPES), centrifuged again, and decanted. The resulting pellet contained a small amount of buffer. Samples (10 μl) of these specimens were spotted onto the elements, and the $\Delta D_r$ was determined accordingly.

Example 1:

Comparative Example

This is an example comparing the method of the present invention with the method of the art described in U.S. Pat. No. 4,525,453, noted above.

TERGITOL 7 anionic surfactant was used to differentiate viable bacteria according to the prior art method. Various concentrations of TERGITOL 7 surfactant were mixed with a 10% glucose solution (50 μl), 3-(4,5-dimethyl-2-thiazolyl)-2,5-diphenyl-2N-tetrazolium bromide (MTT) (25 μl at 5 mg/ml methanol) or a RIND VII dispersion (1.5 ml) and phenazine methosulfate ETA (25 μl at 3 mg/ml methanol). The volume of each test solution was brought to 3 ml with potassium phosphate buffer. A cell suspension (100 μl at about $10^8$ cells/ml) was then added. The solutions were incubated at 37° C. for 15 and 30 minutes in the presence of either E. coli, a gram(−) bacterium, or S. aureus, a gram(+) bacterium. The amount of dye formed was then determined visually, and graded as follows: "0" indicates no dye formation, +/− indicates faint dye formation, 1+ indicates light dye formation, 2+ indicates moderate dye formation, 3+ indicates strong dye formation, and 4+ indicates very strong dye formation.

The results in Table II below indicate that TERGITOL 7 surfactant provided adequate differentiation when MTT was used as the reducible compound, but it failed to do so when RIND VII was used as the reducible compound.

TABLE II

| TERGITOL 7 Surfactant Concentration | MTT | | | | RIND VII | | | |
|---|---|---|---|---|---|---|---|---|
| | E. coli (gram −) | | S. aureus (gram +) | | E. coli (gram −) | | S. aureus (gram +) | |
| | 15' | 30' | 15' | 30' | 15' | 30' | 15' | 30' |
| 0 (Control) | 4+ | 4+ | 4+ | 4+ | 4+ | 4+ | 4+ | 4+ |
| 2% (V/V) | 4+ | 4+ | 0 | 0 | +/− | 1+ | 0 | 0 |
| 1.5% | 4+ | 4+ | 0 | 0 | +/− | 1+ | +/− | 1+ |
| 1% | 4+ | 4+ | 0 | 0 | 2+ | 3+ | 1+ | 3+ |
| 0.5% | 4+ | 4+ | 0 | 0 | 3+ | 4+ | 3+ | 4+ |
| 0.2% | 4+ | 4+ | 0 | 0 | 4+ | 4+ | 4+ | 4+ |

Gramicidin S, a cyclic polypeptide antibiotic, was similarly used with RIND VII in the differentiation of various bacteria which are found in the human urinary tract. Assays were performed as described above. The final concentration of gramicidin S in each test was $10^{-4}$ molar. Control solutions (antibiotic omitted) did not show differentiation. Dye measurements were made at 635 nm and expressed below as the change in optical density ($\Delta$OD) which was corrected for background.

The results, given in Table III below, indicate that gramicidin S selectively inhibits the reduction of the RIND compound by viable gram-positive bacteria but not gram-negative bacteria.

TABLE III

| | Corrected $\Delta$OD (15 Minutes) | |
|---|---|---|
| Bacteria ($7 \times 10^7$/ml) | Control (No Antibiotic) | With Antibiotic ($10^{-4}$ molar) |
| Gram-negative | | |
| E. coli | >2.0 | >2.0 |
| K. pneumoniae | >2.0 | >2.0 |
| P. vulgaris | >2.0 | >2.0 |
| P. aeruginosa | 0.092 | 0.107 |
| P. aeruginosa* | >2.0 | >2.0 |
| Gram-positive | | |
| S. aureus | 0.815 | 0.107 |
| S. faecalis | >2.0 | 0.125 |
| S. pyogenes* | >2.0 | 0.186 |

*Cell concentration of $1.5 \times 10^8$/ml.

Examples 2–3:

Differentiation of Bacteria with Gramicidin S and Tyrocidin

These examples demonstrate the use of two cyclic polypeptide antibiotics, gramicidin S and tyrocidin, to differentiate between viable gram-positive and gram-negative bacteria in solution assays.

Each test solution contained the following: dispersion of RIND XXIX (25 μl) prepared as described above, glucose (400 μl of 10% aqueous solution), tryptose (400 μl of 10% aqueous solution), trimethyl-1,4-benzoquinone ETA (500 μl of 1.5 mg/ml methanol). Aliquots (200 μl) of the mixture were mixed with solutions of the antibiotics (50 μl). The cell suspensions (50 μl) were then added. The final concentration of gramcidin S and tyrocidin were 0.1 mg/ml and 3.3 mg/ml, respectively. The final cell concentration was about $5 \times 10^7$ cells/ml. Cell control solutions contained all reagents except antibiotics. Background controls consisted of both buffer and solution controls. The buffer control contained all reagents except antibiotics and cells. The solution control contained all reagents except cells.

The solutions were incubated at 37° C. for 30 minutes, and the change in fluorescence emission ($\Delta$ fluorescence) was determined as the difference between the readings taken when the solutions were first mixed and then after 30 minutes incubation. Measurements were made in a commercially available MICROFLUOR Reader (available from Dynatech Laboratories, Alexandria, Virginia, U.S.A.), modified with an excitation filter at 540 nm, an emission filter at 620 nm and a Xenon lamp.

The results, shown below in Table IV, indicate that both gramicidin S and tyrocidin can be used with RIND XXIX to differentiate between viable gram-positive and gram-negative bacteria.

TABLE IV

| | $\Delta$ Fluorescence (30 Minutes) | | | |
|---|---|---|---|---|
| | Example 2 | | Example 3 | |
| Microorganism | Cell Control* | Gramicidin S | Cell Control* | Tyrocidin |
| S. aureus (gram +) | >4000 | 0478 | >4000 | 1834 |
| S. faecalis (gram +) | 2583 | 0197 | 2852 | 0880 |
| E. cloacae (gram −) | >4000 | >4000 | >4000 | >4000 |
| E. coli (gram −) | >4000 | >4000 | 3517 | >4000 |

TABLE IV-continued

| | Δ Fluorescence (30 Minutes) | | | |
|---|---|---|---|---|
| | Example 2 | | Example 3 | |
| Microorganism | Cell Control* | Gramicidin S | Cell Control* | Tyrocidin |
| K. pneumoniae (gram —) | 3175 | 3084 | 3005 | >4000 |
| P. vulgaris (gram —) | >4000 | 3491 | 3489 | >4000 |
| P. aeruginosa (gram —) | >4000 | >4000 | >4000 | >4000 |
| Background Control (no cells) | 0097 | 0089 | 0318 | 0792 |

*No antibiotic

Example 4:

Identification of Proteus Species Using Polymixin B Antibiotic

This example illustrates the practice of this invention to identify a Proteus species in solution. Test solutions and cell control solutions were prepared and tested as described in Example 2 and 3 except that polymixin B was used at 0.01 mg/ml of methanol. The final cell concentration was about $5 \times 10^7$ cells/ml.

The results of the tests, shown in Table V below, indicate that polymixin B inhibited all of the gram-negative microorganisms except *Proteus vulgaris* from reducing the RIND XXIX compound. Therefore, polymixin B can be used to differentiate a Proteus species from other gram-negative bacteria.

TABLE V

| | Δ Relative Fluorescence (30 Minutes) | |
|---|---|---|
| Bacteria | Cell Control* | Example 4 |
| P. vulgaris (gram —) | 3968 | 3079 |
| E. cloacae (gram —) | >4000 | 1975 |
| E. coli (gram —) | 3088 | 1245 |
| K. pneumoniae (gram —) | 3553 | 1212 |
| P. aeruginosa (gram —) | 3779 | 1287 |
| Background Control (no cells) | 0231 | 0187 |

*No antibiotic

Example 5:

Comparison Using Various Cyclic Polypeptide Antibiotics

This example compares the use of various cyclic polypeptides in a differentiation assay. Some of the antibiotics tested are within the scope of this invention while others are not.

The cyclic polypeptide antibiotics useful in this invention are those which affect the function of the cytoplasmic membrane as defined in the Reiner reference noted above. Polypeptide antibiotics outside the scope of this invention include mikamycin A and B and virginiamycin which interfere with nucleic acid or protein biosynthesis of microorganisms, and vancomycin and ristocetin which interfere with cell wall biosynthesis.

The following materials were used in this example: stock solutions of RIND IX compound dispersion prepared as described above, glucose (10% in water), trimethyl-1,4-benzoquinone ETA (1.5 mg/ml methanol), and the antibiotics (1 mg/ml in dimethylsulfoxide). *S. aureus* cells were grown as described above. The final cell concentration in the assay mixture was about $4.3 \times 10^8$ cells/ml.

The test were run as follows;

Method 1:

Test solutions were prepared by adding in the order: 1.2 ml of HEPES buffer, 50 μl glucose solution, 1.5 ml of RIND IX dispersion, 100 μl of antibiotic solution, 100 μl of cell suspension and 25 μl of ETA solution.

Control solutions were prepared as described in Examples 2 and 3. Optical density readings (OD) were measured at 635 nm at 0 minutes and after incubation at 37° C. for 30 minutes for test and control solutions, and the change in density (ΔOD) was determined. Table VI below lists the results, expressed as corrected percent inhibition of the reduction of the RIND compound. The corrected percent inhibition is calculated by dividing the difference between the ΔOD obtained from the Cell Control without antibiotic and the ΔOD of the test solution, by ΔOD of the Cell Control without antibiotic. All readings were corrected by subtracting readings of the appropriate background Controls.

Method 2:

Solutions containing 2.9 ml HEPES, 50 μl of the antibiotic solution and 100 μl cell solution were incubated at 37° C. for 30 minutes, centrifuged for 10 minutes and decanted. The resulting pellet was then treated with 1.4 ml HEPES, 50 μl glucose solution, 1.5 ml RIND IX dispersion and 25 μl ETA solution, mixed well and the densities recorded as described above in Method 1. The corrected percent inhibition data was calculated as described in Method 1 above.

The data in Table VI indicates that only gramicidin S, an antibiotic within the scope of this invention, inhibits the ability of *S. aureus*, a gram-positive bacterium, to reduce the RIND compound. The other antibiotics fail to inhibit the reductive capacity of the bacterium.

TABLE VI

| Antibiotic | Test Method | Corrected % Inhibition |
|---|---|---|
| Gramicidin S | 1 | 95.6 |
| Gramicidin S | 2 | 80.0 |
| Mikamycin A & B | 2 | No Inhibition |
| Virginiamycin | 2 | No Inhibition |
| Ristocetin | 1 | No Inhibition |
| Vancomycin | 1 | No Inhibition |

Example 6:

Differentiation of Bacteria Using A Dry Analytical Element

This example demonstrates the practice of this invention using a dry analytical element. The element used had the format and components illustrated below

| Spreading/Reagent Layer | Poly(vinyltoluene-co-p-t-butylstyrene-co-methacrylic acid) beads (66:33:1 weight ratio) | 100–160 g/m² |
|---|---|---|
| | Poly(n-butyl acrylate-co-styrene-co-2-acrylamido-2-methylpropane sulfonic acid) (60:30:10 weight ratio) adhesive | 2–10 g/m² |
| | RIND IX reducible compound | 0.05–0.3 g/m² |
| | Phenazine methosulfate ETA | 0.005–0.2 g/m² |
| | TRITON X-100 surfactant | 1–10 g/m² |
| | Gramicidin S | 0.1–2 g/m² |
| | Glucose | 0.05–1 g/m² |

-continued

| | | |
|---|---|---|
| Subbing Layer | Poly(acrylamido-co-N-vinyl-2-pyrrolidone) (90:10 weight ratio) | 0.1–11 g/m² |
| | ZONYL FSN surfactant | 0.02–2 g/m² |
| | Poly(ethylene terephthalate) Support | |

A Control element was similarly prepared except that gramicidin S was omitted.

The appropriate cell suspension (10 μl) was applied to the spreading/reagent layer of each element. The reflection density ($D_R$) was measured at 640 nm. After 10 minutes of incubation at 37° C., the $D_R$ was again measured, giving a $\Delta D_r$ value. A Control solution (10 μl of either 0.5 molar HEPES or potassium phosphate buffer) was also applied to the elements and the $\Delta D_R$ was similarly determined. The difference between the two $\Delta D_R$ values gives a test value corrected for background. The results, listed in Table VII below, indicate that gramicidin S can be used in an element to differentiate between viable gram-positive and gram-negative bacteria.

TABLE VII

| | Corrected Δ $D_R$ (10 Minutes) | |
|---|---|---|
| Bacteria | Control | Example 6 |
| Gram-negative | | |
| E. coli (5 × 10⁸/ml) | 0.188 | 0.170 |
| K. pneumoniae (3 × 10⁸/ml) | 0.139 | 0.134 |
| P. aeruginosa (3 × 10⁸/ml)* | 0.051 | 0.116 |
| P. vulgaris (5 × 10⁸/ml) | 0.259 | 0.255 |
| Gram-positive | | |
| S. aureus (1 × 10⁹/ml) | 0.176 | 0 |
| S. faecalis (1.5 × 10⁸/ml) | 0.169 | 0.002 |
| S. pyogenes (5 × 10⁸/ml) | 0.150 | 0 |

*25 μl of 10% yeast extract added to 1 ml cell suspension.

Example 7:

Differentiation of Microorganisms Found In Clinical Urine Specimen Using a Dry Element This example demonstrates the practice of this invention to differentiate bacteria found in clinical urine specimens obtained from local hospitals and treated as described in the procedures noted above.

The urine specimens were applied to elements prepared as described in Example 6. A Control element containing no gramicidin S was also used. The elements were then treated and evaluated according to the procedure described in Example 6. The results, listed in Table VIII below, illustrate satisfactory differentiation according to the present invention.

TABLE VIII

| | Corrected Δ $D_R$ (10 Minutes) | |
|---|---|---|
| Bacteria | Control | Example 7 |
| Gram-positive | | |
| Enterococcus (Specimen A) | 0.061 | 0 |
| Enterococcus (Specimen B) | 0.142 | 0.068 |
| Staphylococcus Sp. | 0.142 | 0 |
| Mixed: Staph. Strep. diphtheroids | 0.246 | 0.042 |
| Gram-negative | | |
| E. coli (Specimen C) | 0.159 | 0.288 |
| E. coli (Specimen D) | 0.290 | 0.326 |
| E. coli (Specimen E) | 0.231 | 0.228 |
| Mixed: 2 types gram (−) rods | 0.036 | 0.037 |
| Mixed: 2 types gram (−) rods | 0.383 | 0.351 |
| K. pneumoniae | 0.287 | 0.317 |
| E. coli (Specimen F) | 0.101 | 0.078 |

Example 8 and 9:

Differentiation of Bacteria Using Tetrazolium Salt and Phenolic Dye Reducible Compounds These examples illustrate the differentiation of bacteria using a tetrazolium salt and phenolic dye as the reducible compounds and two cyclic polypeptide antibiotics according to the present invention. The tetrazolium salt was 3-(4,5-dimethyl-2-thiazolyl)-2,5-diphenyl-2H-tetrazolium bromide (MTT) which forms a colored formazan dye when reduced. The phenolic dye was 2,6-dichloroindophenol (DCIP) which forms a colorless species when reduced.

Solutions of the reducible compounds were prepared with the following: HEPES buffer (3 ml, 0.05 molar, pH 7.5), TRITON X-100 nonionic surfactant (1% concentration), glucose (50 μl of 10% in water), tryptose (50 μl of a 10% solution in water), MTT (25 μl of 5 mg/ml methanol) or DCIP (25 μl of 3 mg/ml methanol) and phenazine methosultate ETA (25 μl of 3 mg/ml methanol).

Test solutions were prepared from the following: reducible compound solution from above (200 μl), 50 μl of either gramicidin S solution (6 mg/ml methanol and 9 ml of buffer) or tyrocidin solution (100 mg/ml methanol and 8 ml of buffer) and 50 μl of cell suspension. The final approximate cell concentration in the test solutions was 5×10⁷. The final concentrations of antibiotics were: 0.00625 mg/ml of gramicidin S and 0.825 mg/ml of tyrocidin. Control solutions were prepared as described in Examples 2 and 3. The change in optical density (ΔOD) was determined after 30 minutes at 37° C. at 540 nm for the MTT assay and at 620 nm for the DCIP assay using a commercially available spectrophotometer.

The results of the assays are shown in Tables IX and X below for the differentiations using MTT and DCIP, respectively. The results indicate that reduction of the reducible compounds by gram(+) bacteria is inhibited by the polypeptide antibiotics according to the present invention.

TABLE IX

| | ΔOD, 540 nm after 30 Minutes | | | | |
|---|---|---|---|---|---|
| Bacteria | Gram Stain | Cell Control* | Gramicidin S | Cell Control* | Tyrocidin |
| S. aureus | (+) | 0.949 | 0.177 | 0.747 | 0.113 |
| S. faecalis | (+) | 0.864 | 0.073 | 0.681 | 0.048 |
| E. cloacae | (−) | 1.001 | 0.931 | 0.864 | 0.748 |
| E. coli | (−) | 1.002 | 1.123 | 1.234 | 1.207 |
| K. pneumoniae | (−) | 1.092 | 1.207 | 0.872 | 0.842 |

TABLE IX-continued

| | | ΔOD, 540 nm after 30 Minutes | | | |
|---|---|---|---|---|---|
| Bacteria | Gram Stain | Cell Control* | Gramicidin S | Cell Control* | Tyrocidin |
| P. vulgaris | (−) | 0.995 | 0.841 | 0.806 | 0.778 |
| P. aeruginosa | (−) | 0.996 | 0.955 | 0.812 | 0.692 |
| Background Control (no cells) | | 0.042 | 0.069 | 0.040 | 0.044 |

*No antibiotic

TABLE X

| | | ΔOD, 620 nm after 30 Minutes | | | |
|---|---|---|---|---|---|
| Bacteria | Gram Stain | Cell Control* | Gramicidin S | Cell Control* | Tyrocidin |
| S. aureus | (+) | 0.927 | 0.096 | 1.074 | 0.074 |
| S. faecalis | (+) | 0.901 | 0.066 | 0.947 | 0.048 |
| E. cloacae | (−) | 0.871 | 0.997 | 1.089 | 0.999 |
| E. coli | (−) | 0.935 | 1.042 | 1.028 | 1.054 |
| K. pneumoniae | (−) | 0.973 | 1.062 | 0.962 | 0.819 |
| P. vulgaris | (−) | 0.950 | 1.029 | 1.004 | 0.941 |
| P. aeruginosa | (−) | 1.031 | 1.040 | 1.890 | 0.983 |
| Background Control (no cells) | | 0.076 | 0.046 | 0.093 | 0.021 |

*No antibiotic

The invention has been described in detail with particular reference to preferred embodiments thereof, but it will be understood that variations and modifications can be effected within the spirit and scope of the invention.

We claim:

1. A composition for differentiating between viable gram-positive and gram-negative bacteria comprising:
   (a) a dye or dye precursor capable of being reduced to provide a detectable species by both viable gram-positive and gram-negative bacteria, and
   (b) a cyclic polypeptide antibiotic which affects the cytoplasmic membrane of said bacteria, said antibiotic being present in an amount sufficient to selectively and substantially inhibit the reduction of said reducible dye or dye precursor by said gram-positive bacteria.
   wherein said reducible dye or dye precursor is represented by the structure CAR—(R$^1$) wherein CAR— is a carbocyclic aromatic or quinone nucleus, R$^1$ is a moiety which comprises a shiftable detectable species which is either a chromogen having a first spectral absorption band while attached to said nucleus and a second spectral absorption band when released, or a fluorogen having first spectral absorption and emission bands while attached to said nucleus and second spectral absorption and emission bands when released, and n is 1 or 2.
   provided said reducible dye or dye precursor is capable of being reduced at physiological pH to release said shiftable detectable species, and
   further provided that when R$^1$ is replaced with H, CAR—(H)$_n$ has an E$_{\frac{1}{2}}$ of either at least about +100 mV when measured in water, or of at least about −650 mV when measured in acetonitrile.

2. The composition of claim 1 further comprising an electron transfer agent.

3. The composition of claim 1 wherein said antibiotic is selected from the group consisting essentially of gramicidin S, subtilin and tyrocidin.

4. The composition of claim 1 further comprising a cell nutrient containing useful carbon.

5. The composition of claim 1 wherein said reducible dye precursor has the structure CAR—R$^1$ wherein CAR— is

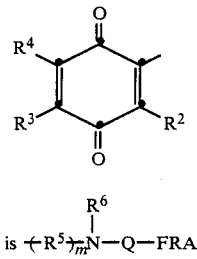

R$^1$ is $(R^5)_{\overline{m}}N$—Q—FRAG,

R$^2$ and R$^4$ are independently hydrogen, alkyl, carbocyclic aryl or an electron withdrawing group having a positive Hammett sigma value, R$^3$ is R$^1$, hydrogen, alkyl, carbocyclic aryl or an electron withdrawing group having a positive Hammett sigma value, provided at least one of R$^2$, R$^3$ and R$^4$ is an electron withdrawing group having a positive Hammett sigma value, or R$^3$ and R$^4$, taken together, represent the atoms necessary to complete a nonaromatic, strained fused carbocyclic 4- to 8-membered ring, R$^5$ is alkylene of 1 or 2 carbon atoms, R$^6$ is alkyl, cycloalkyl, pyridyl, or carbocyclic aryl, Q is carbonyl or thiocarbonyl, FRAG is said shiftable detectable species which provides a detectable species when released from said reducible dye precursor upon reduction by viable bacteria, and m is 0 or 1, provided that when R$^1$ is replaced with H, CAR—H has an E$_{\frac{1}{2}}$ of either at least about +100 mV when measured in water, or of at least about −650 mV when measured in acetonitrile.

6. The composition of claim 5 wherein FRAG provides a chromogen or fluorogen.

7. An analytical element for differentiating between viable gram-positive and viable gram-negative bacteria comprising an absorbent carrier material and containing:

(a) a dye or dye precursor capable of being reduced to provide a detectable species by both viable gram-positive and gram-negative bacteria, and (b) a cyclic polypeptide antibiotic which affects the cytoplasmic membrane of said bacteria, said antibiotic being present in an amount sufficient to selectively and substantially inhibit the reduction of said reducible dye or dye precursor by said gram-positive bacteria.

wherein said reducible dye or dye precursor is represented by the structure CAR—(R$^1$)$_n$ wherein CAR— is a carbocyclic aromatic or quinone nucleus, R$^1$ is a moiety which comprises a shiftable detectable species which is either a chromogen having a first spectral absorption band while attached to said nucleus and a second spectral absorption band when released, or a fluorogen having first spectral absorption and emission bands while attached to said nucleus and second spectral absorption and emission bands when released, and n is 1 or 2, provided said reducible dye or dye precursor is capable of being reduced at physiological pH to release said shiftable detectable species, and further provided that when R$^1$ is replaced with H, CAR—(H)$_n$ has an E$_{\frac{1}{2}}$ of either at least about +100 mV when measured in water, or of at least about −650 mV when measured in acetonitrile.

8. The element of claim 7 further comprising an electron transfer agent.

9. The element of claim 7 wherein said antibiotic is selected from the group consisting essentially of gramicidin S, subtilin and tyrocidin.

10. The element of claim 7 further comprising a cell nutrient containing useful carbon.

11. The element of claim 7 wherein said reducible dye precursor has the structure CAR—R$^1$ wherein CAR— is

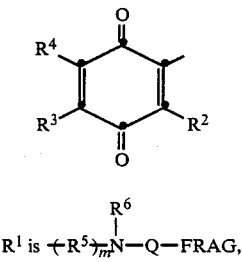

R$^1$ is —(R$^5$)$_m$—N—Q—FRAG,

R$^2$ and R$^4$ are independently hydrogen, alkyl, carbocyclic aryl or an electron withdrawing group having a positive Hammett sigma value, R$^3$ is R$^1$, hydrogen, alkyl, carbocyclic aryl or an electron withdrawing group having a positive Hammett sigma value, provided at least one of R$^2$, R$^3$ and R$^4$ is an electron withdrawing group having a positive Hammett sigma value, or R$^3$ and R$^4$, taken together, represent the atoms necessary to complete a nonaromatic, strained fused carbocyclic 4- to 8-membered ring, R$^5$ is alkylene of 1 or 2 carbon atoms, R$^6$ is alkyl, cycloalkyl, pyridyl, or carbocyclic aryl, Q is carbonyl or thiocarbonyl, FRAG is said shiftable detectable species which provides a detectable species when released from said reducible dye precursor upon reduction by viable bacteria, and m is 0 or 1, provided that when R$^1$ is replaced with H, CAR—H has an E$_{\frac{1}{2}}$ of either at least about +100 mV when measured in water, or of at least about −650 mV when measured in acetonitrile.

12. A method for differentiating between viable gram-positive and gram-negative bacteria comprising the steps of:

A. mixing a first sample of a liquid suspected of containing viable gram-positive or gram-negative bacteria with a dye or dye precursor capable of being reduced to provide a detectable species by both viable gram-positive and gram-negative bacteria, B. mixing a second sample of said liquid with
(a) said dye or dye precursor, and
(b) a cyclic polypeptide antibiotic which affects the cytoplasmic membrane of said bacteria, said antibiotic being present in an amount sufficient to selectively and substantially inhibit the reduction of said reducible dye or dye precursor by said gram-positive bacteria, and C. measuring the difference between said detectable species resulting from steps A and B, wherein said reducible dye or dye precursor is represented by the structure CAR—(R$^1$)$_n$ wherein CAR— is a carbocyclic aromatic or quinone nucleus, R$^1$ is a moiety which comprises a shiftable detectable species which is either a chromogen having a first spectral absorption band while attached to said nucleus and a second spectral absorption band when released, or a fluorogen having first spectral absorption and emission bands while attached to said nucleus and second spectral absorption and emission bands when released, and n is 1 or 2, provided said reducible dye or dye precursor is capable of being reduced at physiological pH to release said shiftable detectable species, and further provided that when R$^1$ is replaced with H, CAR—(H)$_n$ has an E$_{\frac{1}{2}}$ of either at least about +100 mV when measured in water, or of at least about −650 mV when measured in acetonitrile.

13. The method of claim 12 wherein said liquid is also mixed with an electron transfer agent and a cell nutrient containing useful carbon.

14. The method of claim 12 wherein said antibiotic is selected from the group consisting essentially of gramicidin S, subtilin and tyrocidin.

15. The method of claim 12 wherein said detectable species is determined colorimetrically or fluorometrically.

16. The method of claim 12 wherein said reducible dye precursor has the structure CAR—R$^1$ wherein CAR— is

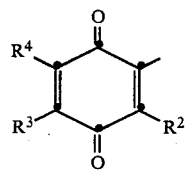

-continued

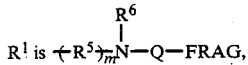

R² and R⁴ are independently hydrogen, alkyl, carbocyclic aryl or an electron withdrawing group having a positive Hammett sigma value, R³ is R¹, hydrogen, alkyl, carbocyclic aryl or an electron withdrawing group having a positive Hammett sigma value, provided at least one of R², R³ and R⁴ is an electron withdrawing group having a positive Hammett sigma value, or R³ and R⁴, taken together, represent the atoms necessary to complete a nonaromatic, strained fused carbocyclic 4- to 8-membered ring, R⁵ is alkylene of 1 or 2 carbon atoms, R⁶ is alkyl, cycloalkyl, pyridyl, or carbocyclic aryl, Q is carbonyl or thiocarbonyl, FRAG is said shiftable detectable species which provides a detectable species when released from said reducible dye precursor upon reduction by viable bacteria, and m is 0 or 1, provided that when R¹ is replaced with H, CAR—H has an $E_{\frac{1}{2}}$ of either at least about +100 mV when measured in water, or of at least about −650 mV when measured in acetonitrile.

17. The method of claim 12 for differentiation of viable human urinary tract gram-positive and gram-negative bacteria.

18. A composition for the differentiation of viable Proteus bacteria from other viable gram-negative bacteria comprising:
(a) a dye or dye precursor capable of being reduced to provide a detectable species by viable gram-negative bacteria, and
(b) polymixin B present in an amount sufficient to selectively and substantially inhibit the reduction of said reducible dye or dye precursor by said gram-negative bacteria other than Proteus genera.

19. An analytical element for differentiating between viable Proteus bacteria and other viable gram-negative bacteria comprising an absorbent carrier material and containing:
(a) a dye or dye precursor capable of being reduced to provide a detectable species by viable gram-negative bacteria, and
(b) polymixin B present in an amount sufficient to selectively and substantially inhibit the reduction of said reducible dye or dye precursor by said gram-negative bacteria other than Proteus species.

20. A method for differentiating between viable Proteus bacteria and other viable gram-negative bacteria comprising the steps of:
A. mixing a first sample of a liquid suspected of containing viable Proteus or other gram-negative bacteria with a dye or dye precursor capable of being reduced to provide a detectable species by both viable Proteus and other gram-negative bacteria,
B. mixing a second sample of said liquid with
(a) a said dye or dye precursor, and
(b) polymixin B present in an amount sufficient to selectively and substantially inhibit the reduction of said reducible dye or dye precursor by said other gram-negative bacteria, and
C. measuring the difference between said detectable species resulting from steps A and B.

21. A composition for differentiating between viable gram-positive and gram-negative bacteria comprising:
(a) a dye or dye precursor capable of being reduced to provide a detectable species by both viable gram-positive and gram-negative bacteria, and
(b) either antibiotic gramicidin S or tyrocidin, said antibiotic being present in an amount sufficient to selectively and substantially inhibit the reduction of said reducible dye or dye precursor by said gram-positive bacteria.

22. An analytical element for differentiating between viable gram-positive and viable gram-negative bacteria comprising an absorbent carrier material and containing:
(a) a dye or dye precursor capable of being reduced to provide a detectable species by both viable gram-positive and gram-negative bacteria, and
(b) either antibiotic gramicidin S or tyrocidin, said antibiotic being present in an amount sufficient to selectively and substantially inhibit the reduction of said reducible dye or dye precursor by said gram-positive bacteria.

23. A method for differentiating between viable gram-positive and gram-negative bacteria comprising the steps of:
A. mixing a first sample of a liquid suspected of containing viable gram-positive or gram-negative bacteria with a dye or dye precursor capable of being reduced to provide a detectable species by both viable gram-positive and gram-negative bacteria,
B. mixing a second sample of said liquid with
(a) said dye or dye precursor, and
(b) either antibiotic gramicidin S or tyrocidin, said antibiotic being present in an amount sufficient to selectively and substantially inhibit the reduction of said reducible dye or dye precursor by said gram-positive bacteria, and
C. measuring the difference between said detectable species resulting step A and B.

* * * * *